US008318644B2

(12) United States Patent
Kamimura et al.

(10) Patent No.: US 8,318,644 B2
(45) Date of Patent: Nov. 27, 2012

(54) LUBRICATING OIL

(75) Inventors: Hideto Kamimura, Ichihara (JP); Shigeyuki Mori, Morioka (JP)

(73) Assignees: Idemitsu Kosan Co., Ltd., Tokyo (JP); Shigeyuki Mori, Morioka-shi (JP)

( * ) Notice: Subject to any disclaimer, the term of this patent is extended or adjusted under 35 U.S.C. 154(b) by 1256 days.

(21) Appl. No.: 10/570,666

(22) PCT Filed: Oct. 8, 2004

(86) PCT No.: PCT/JP2004/014942

§ 371 (c)(1),
(2), (4) Date: Mar. 6, 2006

(87) PCT Pub. No.: WO2005/035702

PCT Pub. Date: Apr. 21, 2005

(65) Prior Publication Data

US 2007/0027038 A1 Feb. 1, 2007

(30) Foreign Application Priority Data

Oct. 10, 2003 (JP) ................................ 2003-352264
Apr. 21, 2004 (JP) ................................ 2004-125491
Apr. 26, 2004 (JP) ................................ 2004-129813
Aug. 5, 2004 (JP) ................................ 2004-229457

(51) Int. Cl.

| | |
|---|---|
| ***C07C 317/22*** | (2006.01) |
| ***C10M 141/10*** | (2006.01) |
| ***C10M 133/06*** | (2006.01) |
| ***C07D 207/26*** | (2006.01) |
| ***C07D 233/14*** | (2006.01) |

(52) U.S. Cl. ........ 508/244; 508/262; 508/268; 508/283; 508/302; 508/421; 508/545

(58) Field of Classification Search .................. 508/244, 508/262, 268, 283, 302, 421, 545
See application file for complete search history.

(56) References Cited

U.S. PATENT DOCUMENTS

| | | | | |
|---|---|---|---|---|
| 5,603,861 | A * | 2/1997 | Umamori et al. ............ | 252/78.3 |
| 5,827,602 | A | 10/1998 | Koch et al. | |
| 7,153,974 | B2 | 12/2006 | Schmidt et al. | |
| 7,297,289 | B2 * | 11/2007 | Sato et al. .................... | 252/62.2 |
| 2002/0015884 | A1 | 2/2002 | Schmidt et al. | |
| 2004/0035293 | A1 * | 2/2004 | Davis, Jr. ........................ | 95/140 |

FOREIGN PATENT DOCUMENTS

| | | |
|---|---|---|
| EP | 1162204 | 12/2001 |
| JP | 2000-130687 | 5/2000 |
| JP | 2002-25610 | 1/2002 |
| JP | 2002-187893 | 7/2002 |
| WO | 02/080196 | 10/2002 |
| WO | 03/035609 | 5/2003 |
| WO | WO 03/086605 A2 | 10/2003 |

OTHER PUBLICATIONS

U.S. Appl. No. 11/913,182, filed Oct. 31, 2007, Kamimura, et al.
Ye, Chengfeng et al., "Room-temperature ionic liquids: a novel versatile lubricant", Chemical Communications, No. 21, pp. 2244-2245, 2001.
Liu, W. et al., "Tribological behavior of sialon ceramics sliding against steel lubricated by fluorine-containing oils", Tribology International, vol. 35, No. 8, pp. 503-509, 2002.
Reich, Ronald A. et al., "Base Oil Properties of Ionic Liquids", Lubrication Engineering, vol. 59, No. 7, pp. 16 to 21, 2003.
Weimin Liu, et al., "Tribological Performance of Room-Temperature Ionic Liquids as Lubricant" TRIBOLOGY Letters; vol. 13, No. 2; (pp. 81-85); Aug. 2002; XP002382044.
Hiroyuki Ohno, et al., "A New Type of Polymer Gel Electrolyte: Zwitterionic Liquid/Polar Polymer Mixture" Electrochimica Acta; vol. 48; (pp. 2079-2083); 2003; XP-002475059.
Masahiro Yoshizawa, et al., "Ion Conduction in Zwitterionic-Type Molten Salts and their Polymers" The Journal of Materials Chemistry; vol. 11; (pp. 1057-1062); 2001; XP-002475060.
Pierre Bonhote, et al., "Hydrophobic, Highly Conductive Ambient-Temperature Molten Salts" Inorganic Chemistry; (pp. 1168-1178); 1996; XP-002475124.
Chen Yunxia, et al., "Tribological Performace of an Ionic Liquid as a Lubricant for Steel/Aluminium Contacts", J. Synthetic Lubrication 20-3, Oct. 2003, pp. 217-225.

* cited by examiner

*Primary Examiner* — Prem C Singh
*Assistant Examiner* — Vishal Vasisth
(74) *Attorney, Agent, or Firm* — Oblon, Spivak, McClelland, Maier & Neustadt, L.L.P.

(57) ABSTRACT

The invention provides a lube oil which exhibits low vapor pressure despite having low viscosity, is non-flammable, exhibits excellent heat resistance, has tribological characteristics equivalent to those of conventional hydrocarbon-based lube oils, and can be used for a long time under very severe conditions such as high temperature and vacuum.

The lube oil contains, as a base oil, an ionic liquid formed of a cation and an anion and having an ion concentration of 1 $mol/dm^3$ or more.

10 Claims, No Drawings

LUBRICATING OIL

This application is a 371 of PCT/JP04/14942, filed Oct. 8, 2004.

TECHNICAL FIELD

The present invention relates to a lube oil and, more particularly, to a lube oil which exhibits low vapor pressure despite having low viscosity, is not flammable, exhibits higher heat resistance, has tribological characteristics equivalent to those of conventional hydrocarbon-based lube oils, and can be used for a long time under very severe conditions such as high temperature and vacuum. The lube oil is suitably used in internal combustion engines, torque converters, fluid couplings, radial bearings, rolling bearings, oil-retaining bearings, fluid bearings, compressors, chain drives, gears, oil hydraulic circuits, vacuum pumps, clock parts, hard disk apparatuses, refrigerators, cutting, rolling, metal drawing, form rolling, forging, heat treatment, heat media, cooling media, coolants, washing, shock absorbers, corrosion prevention, brake members, sealing devices, and aerospace apparatuses such as aircraft and artificial satellites. The invention also relates to a method for regulating lubrication characteristics of the lube oil and to a lube oil regulating apparatus employing the lube oil.

BACKGROUND ART

Recent developments in machine technology have realized higher output and rotation rate of engines and motors, and as a result, demand has arisen for a high-performance lube oil which endures severe use conditions. In addition, in order to cope with energy and environmental problems, such a lube oil is required to have fuel consumption reduction effects and energy saving effects as essential performance characteristics. Recently, the lube oil must further have a long-life (long-drain) performance from the viewpoint of resource savings.

Under such circumstances, in the future, the lube oil is required to have as low a viscosity as possible for reducing viscosity resistance which would otherwise cause power loss; sufficient heat resistance; and durability under long-term use conditions.

Generally, lube oil is an organic material predominantly composed of hydrocarbon. Therefore, when viscosity of the lube oil is reduced, vapor pressure of the oil inevitably increases, resulting in loss of the lube oil via evaporation and increasing flammability. Particularly when the lube oil is employed as, for example, hydraulic fluid in facilities where high-temperature objects are handled; e.g., machines in an iron mill, the lube oil must have non-flammability, from the viewpoint of fire prevention. In precision motors employed in information-related apparatuses (e.g., hard disk apparatuses) which have been developed in recent years, a lube oil having resistance to evaporation and diffusion is demanded in order to minimize adverse effect on other precision apparatuses placed therearound.

In order to solve such problems, hitherto, fatty acid esters, silicone oils, and fluorocarbon-based oils such as perfluoropolyether have been proposed as lube oils which have low viscosity and high heat resistance despite low vapor pressure. However, these proposed materials have drawbacks. Specifically, fatty acid esters have poor water resistance, due to the ester structure, which is highly susceptible to hydrolysis. Although silicone oils and fluorocarbon-based oils have excellent heat resistance and water resistance, these oils exhibit poor lubricity as compared with conventional hydrocarbon-based lube oils. Thus, there has never been provided a lube oil totally meeting strict demands which are to be required more and more in the future.

Meanwhile, in recent years, it has been reported that, among organic ionic liquids each being formed of a cation and an anion, a class of ethylimidazolium salts having a variety of anion moieties exhibit excellent thermal stability and high ionic conductivity and assume liquid stable in air (see, for example, Patent Document 1). Thereafter, interest in these ionic liquids has grown rapidly, and extensive studies on the liquids have been carried out. A variety of applications such as electrolyte in solar cells (see, for example, Non-Patent Document 1) and solvents for extraction/separation and reaction have been envisaged on the basis of various characteristics of the ionic liquids including thermal stability (volatilization resistance and non-inflammability), high ion density (high ionic conductivity), large heat capacity, and low viscosity. However, there have never been reported cases in which the aforementioned organic ionic liquids are employed as lube base oils.

In ionic liquid, molecules thereof are bonded via ionic bonds, which are stronger than intramolecular forces as found in molecular liquid. Therefore, ionic liquid is resistant to volatilization, is non-flammable, and is stable against heat and oxidation. In addition, since the ionic liquid exhibits low volatility despite having low viscosity, and has excellent heat resistance, it may be the only lube oil that would meet strict demands required in the future. However, physical properties of ionic liquid greatly depend upon ionic bonds between molecules. Thus, differing from the case of molecular liquid such as liquid hydrocarbons, physical properties of ionic liquid are difficult to predict from the molecular structure thereof, and properties such as viscosity, viscosity index, and pour point cannot readily be controlled through modification of the molecular structure. In other words, design and synthesis of an ionic liquid compound having target physical properties are difficult, which is problematic.

In addition, ionic liquid per se is a salt formed of a cation and an anion. Therefore, an ionic liquid formed of a certain cation-anion combination is dissolved in water in an arbitrary amount (see, for example, Non-Patent Document 2). Although such an ionic liquid does not decompose or cause corrosion under anhydrous conditions, the ionic liquid absorbs water under hydrous conditions and may decompose or cause corrosion. Among ionic liquids having excellent heat resistance, species having an ion (e.g., an imidazolinium ion) are oxidative or highly susceptible to reduction decomposition (see, for example, Non-Patent Document 3), and those having another ion (e.g., $BF_4^-$ or $Cl^-$) have toxicity and impose a heavy environmental load. Thus, in order to obtain a lube oil meeting a strict demand, rigorous selection of constituent ions is preferred.

Furthermore, ionic liquid, which is formed of a positively charged cation and a negatively charged anion, also has electrical characteristics; e.g., alignment in accordance with an electric field and formation of an electric double-layer on an electrode surface. By virtue of the aforementioned electrical characteristics, when an electric field is applied to a lubrication site where ionic liquid is present, electrical characteristics will be developed, possibly varying tribological characteristics to a certain degree.

There have conventionally been disclosed methods for regulating friction including application of an electric field to a system employing a lube oil. For example, some methods employ a dispersion-type electrical viscous fluid in which solid particles are dispersed in a liquid medium (see, for example, Patent Documents 2 and 3), and others employ a homogeneous electrical viscous fluid which is formed of a liquid crystal homogeneous solvent (see, for example, Patent Document 4). All these methods regulate tribological conditions through modification of physical properties of electrical viscous fluid (i.e., increasing viscosity). Therefore, when friction conditions such as shear rate and load become too severe to overcome, the effect commensurate with increase in viscosity often fails to be attained.

[Patent Document 1]
Japanese Patent Application Laid-Open (kokai) No. 2003-31270
[Patent Document 2]
Japanese Patent Application Laid-Open (kokai) No. Heisei 5(1993)-25488
[Patent Document 3]
Japanese Patent Application Laid-Open (kokai) No. 2000-1694
[Patent Document 4]
Japanese Patent Application Laid-Open (kokai) No. 2000-130687
[Non-Patent Document 1]
J. Chem. Soc., Chem. Commun., 965(1992)
[Non-Patent Document 2]
"Ionic Liquids: The Front and Future of Material Development," CMC Publishing CO., LTD.
[Non-Patent Document 3]
"M. Ui, Curr. Top. Electrochem., 7, 49(2000)

DISCLOSURE OF THE INVENTION

Problems to be Solved by the Invention

The present invention has been conceived under the aforementioned circumstances. Thus, an object of the present invention is to provide a lube oil which exhibits low vapor pressure despite having low viscosity, is non-flammable, exhibits excellent heat resistance, has tribological characteristics equivalent to those of conventional hydrocarbon-based lube oils, and can be used for a long time under very severe conditions such as high temperature and vacuum. Another object of the invention is to provide, in a simple manner, a lube oil having remarkably improved physical characteristics (viscosity index, pour point, etc.) or a non-toxic and non-corrosive lube oil. Still another object of the invention is to provide a method for regulating lubrication characteristics of the lube oils. Yet another object of the invention is to provide a lube oil regulating apparatus employing any of the lube oils.

Means for Solving the Problems

The present inventors have carried out extensive studies in order to attain the aforementioned objects, and have found that the objects can be attained through employment, as a base oil, of an ionic liquid formed of a cation and an anion. The present invention has been accomplished on the basis of this finding.

Accordingly, the present invention provides a lube oil, a method for regulating lubricating characteristics, and a lube oil regulating apparatus, as described below.

1. A lube oil comprising, as a base oil, an ionic liquid formed of a cation and an anion and having an ion concentration of 1 mol/dm$^3$ or more.
2. A lube oil as described in 1 above, wherein the ionic liquid has a total acid value of 1 mgKOH/g or less, and the lube oil contains the ionic liquid as a base oil, in an amount of 50 to 100 mass %.
3. A lube oil as described in 1 or 2 above, wherein the ionic liquid is represented by the following formula:

$$(Z^{p+})_k(A^{q-})_m$$

(wherein $Z^{p+}$ represents a cation; $A^{q+}$ represents an anion; each of p, q, k, m, p×k, and q×m is an integer of 1 to 3, with the relationship p×k=q×m being satisfied; and, when k or m is 2 or more, Z or A may be identical to or different from each other).

4. A lube oil as described in 3 above, wherein the ionic liquid is represented by the formula $Z^+A^-$ (wherein $Z^+$ represents a cation and $A^-$ represents an anion) and has a total acid value of 1 mgKOH/g or less, and the lube oil contains the ionic liquid as a base oil, in an amount of 50 to 100 mass %.
5. A lube oil as described in 4 above, wherein the ionic liquid is a mixture of two or more ionic liquids.
6. A lube oil as described in 5 above, wherein the mixture contains one $Z^+$ species and two or more $A^-$ species, two or more $Z^+$ species and one $A^-$ species, or two or more $Z^+$ species and two or more $A^-$ species.
7. A lube oil as described in any of 4 to 6 above, wherein the cation ($Z^+$) forming the ionic liquid is represented by any of the following formulas:

[F1]

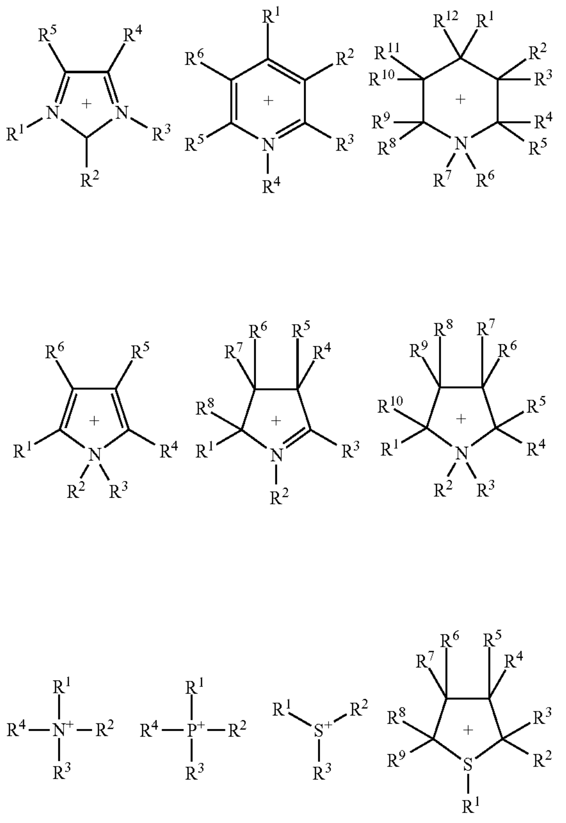

(wherein each of $R^1$ to $R^{12}$, which may be identical to or different from one another, represents a group selected from among a hydrogen atom, C1 to C18 alkyl groups which may each have an ether bond, and C1 to C18 alkoxy groups).

8. A lube oil as described in 7 above, wherein the cation ($Z^+$) forming the ionic liquid is represented by any of the following formulas:

[F2]

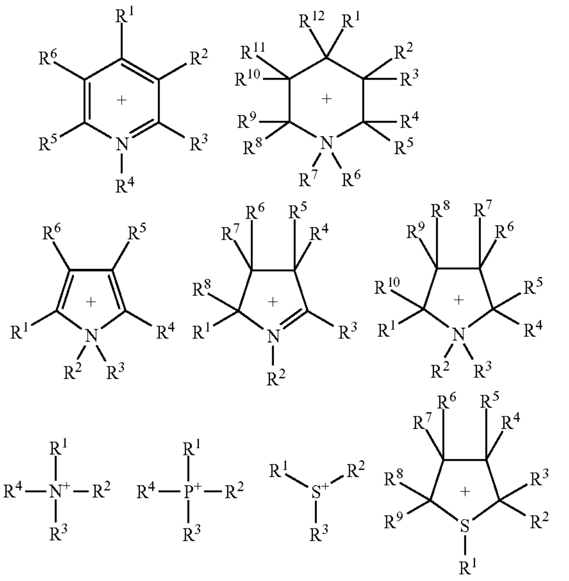

(wherein each of $R^1$ to $R^{12}$, which may be identical to or different from one another, represents a group selected from among a hydrogen atom, C1 to C18 alkyl groups which may each have an ether bond, and C1 to C18 alkoxy groups).

9. A lube oil as described in any of 4 to 8 above, wherein the anion ($A^-$) forming the ionic liquid is selected from among $BF_4^-$, $PF_6^-$, $C_nH_{(2n+1)}OSO_3^-$, $(C_nF_{(2n+1-x)}H_x)SO_3^-$, $(C_nF_{(2n+1-x)}H_x)COO^-$, $NO_3^-$, $CH_3SO_3^-$, $(CN)_2N^-$, $HSO_3^-$, $C_6H_5SO_3^-$, $CH_3(C_6H_4)SO^3{}_-$, $I^-$, $I_3^-$, $F(HF)_n^-$, $((C_nF_{(2n+1-x)}H_x)Y^1O_z)_3C^-$, $((C_nF_{(2n+1-x)}H_x)Y^1O_z)_2N^-$ (wherein $Y^1$ represents a carbon atom or a sulfur atom; when a plurality of $Y^1$s are present, these may be identical to or different from one another; a plurality of $(C_nF_{(2n+1-x)}H_x)Y^1O_z$ groups may be identical to or different from one another); n is an integer of 1 to 6; x is an integer of 0 to 13; and z is an integer of 1 to 3 when $Y^1$ is a carbon atom and 0 to 4 when $Y^1$ is a sulfur atom), $B(C_mY^2{}_{(2m+1)})_4^-$, $P(C_mY^2{}_{(2m+1)})_6^-$ (wherein $Y^2$ is a hydrogen atom or a fluorine atom; when a plurality of $Y^2$s are present, these may be identical to or different from one another; a plurality of $(C_mY^2{}_{(2m+1)})$ groups may be identical to or different from one another); and m is an integer of 0 to 6), and anions represented by the following formula:

[F3]

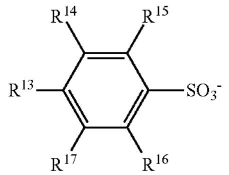

(wherein each of $R^{13}$ to $R^{17}$, which may be identical to or different from one another, represents a group selected from a hydrogen atom and $(C_nF_{(2n+1-x)}H_x)$; and n and x have the same meanings as defined above).

10. A lube oil as described in 9 above, wherein the anion ($A^-$) forming the ionic liquid is selected from among $PF_6^-$, $C_nH_{(2n+1)}OSO_3^-$, $(C_nF_{(2n+1-x)}H_x)SO_3^-$, $(C_nF_{(2n+1-x)}H_x)COO^-$, $NO_3^-$, $CH_3SO_3^-$, $(CN)_2N^-$, $HSO_3^-$, $((C_nF_{(2n+1-x)}H_x)Y^1O_z)_2N^-$ (wherein $Y^1$ represents a carbon atom or a sulfur atom; when a plurality of $Y^1$s are present, these may be identical to or different from one another; n is an integer of 1 to 6; x is an integer of 0 to 13; and z is an integer of 1 to 3 when $Y^1$ is a carbon atom and 0 to 4 when $Y^1$ is a sulfur atom), and anions represented by the following formula:

[F4]

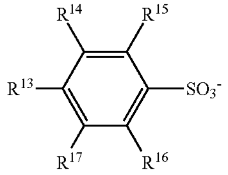

(wherein each of $R^{13}$ to $R^{17}$, which may be identical to or different from one another, represents a group selected from a hydrogen atom and $(C_nF_{(2n+1-x)}H_x)$; and n and x have the same meanings as defined above).

11. A lube oil as described in 10 above, wherein the anion ($A^-$) forming the ionic liquid is selected from among $C_nH_{(2n+1)}OSO_3^-$, $(C_nF_{(2n+1-x)}H_x)SO_3^-$, $(C_nF_{(2n+1-x)}H_x)COO^-$, $NO_3^-$, $CH_3SO_3^-$, $(CN)_2N^-$, $HSO_3^-$, (wherein n is an integer of 1 to 6; and x is an integer of 0 to 13), and anions represented by the following formula:

[F5]

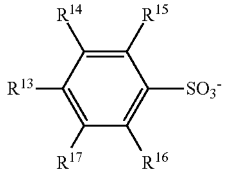

(wherein each of $R^{13}$ to $R^{17}$, which may be identical to or different from one another, represents a group selected from a hydrogen atom and $(C_nF_{(2n+1-x)}H_x)$; and n and x have the same meanings as defined above).

12. A lube oil as described in any of 4 to 11 above, wherein the ionic liquid does not contain a cation represented by the following formula:

[F6]

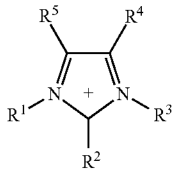

(wherein each of $R^1$ to $R^5$, which may be identical to or different from one another, represents a group selected from among a hydrogen atom, C1 to C18 alkyl groups which may each have an ether bond, and C1 to C18 alkoxy groups), $F^-$, $Cl^-$, $Br^-$, or $BF_4^-$.

13. A lube oil comprising, as a base oil, an ionic liquid formed of a zwitter ion in which a cation and an anion are linked via a covalent bond and which has a total acid value of 1 mgKOH/g or less, in an amount of 50 to 100 mass %.

14. A lube oil as described in 13 above, wherein the ionic liquid is represented by the following formula:

[F7]

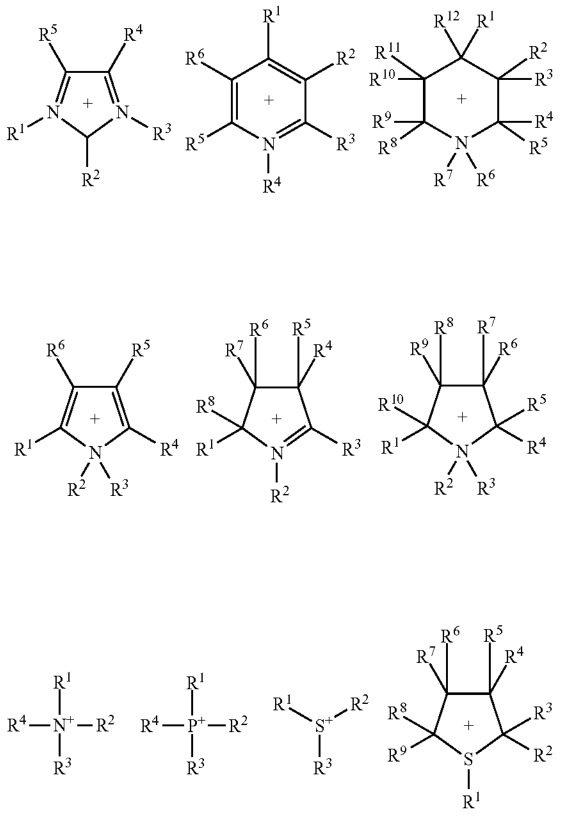

(wherein each of $R^1$ to $R^{12}$, which may be identical to or different from one another, represents a group selected from among a hydrogen atom, C1 to C18 alkyl groups which may each have an ether bond, and C1 to C18 alkoxy groups; and at least one of $R^1$ to $R^{12}$ is $—(CH_2)_n—SO_3^-$ or $—(CH_2)_n—COO^-$ (wherein n is an integer of 0 or greater such that the number of carbon atoms of each alkyl group falls within a range of 1 to 18)).

15. A lube oil as described in any of 1 to 14 above, wherein the ionic liquid has a kinematic viscosity of 1 to 1,000 $mm^2/s$ as determined at 40° C.

16. A lube oil as described in any of 1 to 15 above, wherein the ionic liquid has a pour point of −10° C. or lower.

17. A lube oil as described in any of 1 to 16 above, wherein the ionic liquid has a viscosity index of 80 or more.

18. A lube oil as described in any of 1 to 17 above, wherein the ionic liquid has a flash point of 200° C. or higher.

19. A lube oil as described in any of 1 to 18 above, which contains at least one member selected from an antioxidant and an extreme pressure agent.

20. A lube oil as described in any of 1 to 18 above, which has a water content of 500 ppm by mass or less on the basis of the lube oil.

21. A method for regulating lubrication characteristics, characterized in that the method comprises applying an electric field to a lube oil as recited in any of 1 to 20 above.

22. A lubrication characteristic regulating apparatus for regulating the lubrication characteristic of a contact region between two lubrication member, characterized in that the apparatus is adapted, in use, for interacting with a lube oil as recited in any of 1 to 20 above which is introduced into said contact region, and which apparatus comprises a pair of electrodes which are placed so as to sandwich the contact region, the electrodes being in contact or not in contact with the lubrication members and being provided for applying an electric field to the contact region.

Effects of the Invention

The lube oil of the present invention, containing an ionic liquid serving as a base oil, exhibits low vapor pressure despite having low viscosity, is not inflammable, exhibits excellent heat resistance, has tribological characteristics equivalent to those of conventional hydrocarbon-based lube oils, and can be used for a long time under very severe conditions such as high temperature and vacuum. The invention also provides, in a simple manner, a lube oil having remarkably improved physical characteristics (viscosity index, pour point, etc.) or a non-toxic and non-corrosive lube oil. The invention also provides a method for regulating lubrication characteristics of the lube oils and a lube oil characteristics regulating apparatus employing any of the lube oil.

BEST MODES FOR CARRYING OUT THE INVENTION

The lube oil of the present invention contains, as a base oil, an ionic liquid formed of a cation and an anion and having an ion concentration of 1 $mol/dm^3$ or more as measured at 20° C. In order to attain strong ionic atmosphere and electrostatic interaction from sole cations and anions without employing water or other solvents, the ion concentration is required to be 1 $mol/dm^3$ or more, preferably 1.5 $mol/dm^3$ or more, more preferably 2 $mol/dm^3$ or more. As used herein, the concept "ion concentration" refers to a value calculated from the following relationship:

[density of ionic liquid ($g/cm^3$)/molecular weight (MW) of ionic liquid (g/mol)]×1000.

Preferably, the lube oil of the present invention contains an ionic liquid having a total acid value of 1 mgKOH/g or less as a base oil in an amount of 50 to 100 mass %. The ionic liquid which may be employed is represented by the following formula:

$$(Z^{p+})_k(A^{q-})_m$$

(wherein $Z^{p+}$ represents a cation; $A^{q-}$ represents an anion; each of p, q, k, m, p×k, and q×m is an integer of 1 to 3, with the relationship p×k=q×m being satisfied; and, when k or m is 2 or more, Z or A may be identical to or different from each other). In the present invention, p, q, k, or m in the above formula is preferably 2 or less. More preferably, the lube oil contains an ionic liquid is represented by the formula $Z^+A^-$ (wherein $Z^+$ represents a cation and $A^-$ represents an anion); i.e., the case in which p, q, k, and m are 1 in the above formula, in an amount of 50 to 100 mass %. The lube oil of the present invention preferably has an ionic liquid content of 70 to 100 mass %, more preferably 90 to 100 mass %.

The aforementioned cation ($Z^+$) is preferably represented by any of the following formulas:

[F8]

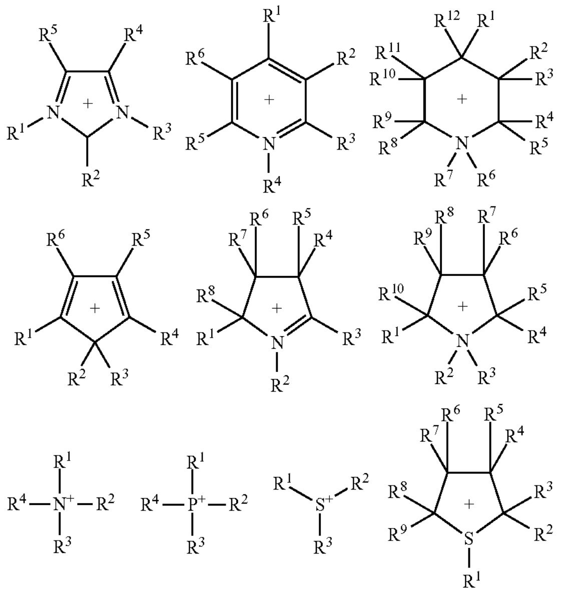

(wherein each of $R^1$ to $R^{12}$, which may be identical to or different from one another, represents a group selected from among a hydrogen atom, C1 to C18 alkyl groups which may each have an ether bond, and C1 to C18 alkoxy groups).

Examples of the C1 to C18 alkyl group which may have an ether bond present as any of $R^1$ to $R^{12}$ include methyl, ethyl, n-propyl, isopropyl, n-butyl, isobutyl, sec-butyl, tert-butyl, pentyl groups, hexyl groups, heptyl groups, octyl groups, and 2-methoxyethyl. Examples of the C1 to C18 alkoxy group include methoxy, ethoxy, n-propoxy, isopropoxy, n-butoxy, isobutoxy, sec-butoxy, tert-butoxy, pentoxy groups, heptoxy groups, and octoxy groups. In the present invention, C1 to C10 alkyl groups are preferred.

Among the aforementioned cations ($Z^+$), the following species are more preferred:

[F9]

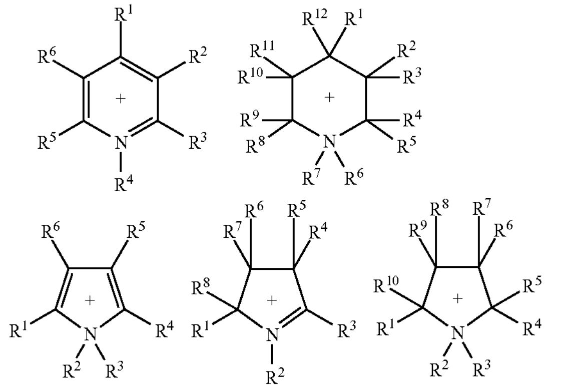

-continued

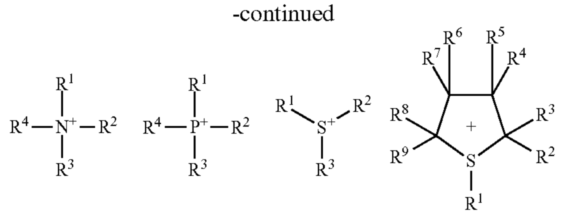

(wherein $R^1$ to $R^{12}$ have the same meanings as defined above).

Examples of preferred anions ($A^-$) include $BF_4^-$, $PF_6^-$, $C_nH_{(2n+1)}OSO_3^-$, $(C_nF_{(2n+1-x)}H_x)SO_3^-$, $(C_nF_{(2n+1-x)}H_x)COO^-$, $NO_3^-$, $CH_3SO_3^-$, $(CN)_2N^-$, $HSO_3^-$, $C_6H_5SO_3^-$, $CH_3(C_6H_4)SO_3^-$, $I^-$, $I_3^-$, $F(HF)_n^-$, $((C_nF_{(2n+1-x)}H_x)Y^1O_z)_3C^-$, $((C_nF_{(2n+1-x)}H_x)Y^1O_z)_2N^-$ (wherein $Y^1$ represents a carbon atom or a sulfur atom; when a plurality of $Y^1$s are present, these may be identical to or different from one another; a plurality of $(C_nF_{(2n+1-x)}H_x)Y^1O_z$ groups may be identical to or different from one another); n is an integer of 1 to 6; x is an integer of 0 to 13; and z is an integer of 1 to 3 when $Y^1$ is a carbon atom and 0 to 4 when $Y^1$ is a sulfur atom), $B(C_mY^2_{(2m+1)})_4^-$, $P(C_mY^2_{(2m+1)})_6^-$ (wherein $Y^2$ is a hydrogen atom or a fluorine atom; when a plurality of $Y^2$s are present, these may be identical to or different from one another; a plurality of $(C_mY^2_{(2m+1)})$ groups may be identical to or different from one another); and m is an integer of 0 to 6), and anions represented by the following formula:

[F10]

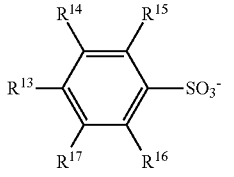

(wherein each of $R^{13}$ to $R^{17}$, which may be identical to or different from one another, represents a group selected from a hydrogen atom and $(C_nF_{(2n+1-x)}H_x)$; and n and x have the same meanings as defined above). Of these, anions containing a fluorine atom are particularly preferred.

Among the aforementioned anions ($A^-$), more preferred anions are $PF_6^-$, $C_nH_{(2n+1)}OSO_3^-$, $(C_nF_{(2n+1-x)}H_x)SO_3^-$, $(C_nF_{(2n+1-x)}H_x)COO^-$, $NO_3^-$, $CH_3SO_3^-$, $(CN)_2N^-$, $HSO_3^-$, $((C_nF_{(2n+1-x)}H_x)Y^1O_z)_2N^-$ (wherein $Y^1$ represents a carbon atom or a sulfur atom; when a plurality of $Y^1$s are present, these may be identical to or different from one another; n is an integer of 1 to 6; x is an integer of 0 to 13; and z is an integer of 1 to 3 when $Y^1$ is a carbon atom and 0 to 4 when $Y^1$ is a sulfur atom), and anions represented by the above formula. Particularly preferred anions are $C_nH_{(2n+1)}OSO_3^-$, $(C_nF_{(2n+1-x)}H_x)SO_3^-$, $(C_nF_{(2n+1-x)}H_x)COO^-$, $NO_3^-$, $CH_3SO_3^-$, $(CN)_2N^-$, $HSO_3^-$, (wherein n is an integer of 1 to 6; and x is an integer of 0 to 13), and anions represented by the above.

Examples of the ionic liquid represented by the formula $(Z^{p+})_k(A^{q-})$ serving as a base oil include those represented by the following formula:

[F11]

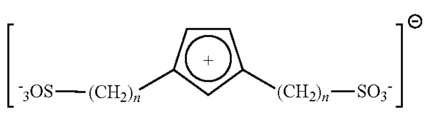

(wherein M represents a cation selected from among $H^+$, $Li^+$, $Na^+$, $K^+$, $Pb^+$, and $Cs^+$; and n is an integer of 0 to 18).

Specific examples of the ionic liquid represented by the formula $Z^+A^-$ serving as a base oil include 1-butyl-3-methylimidazolium tetrafluoroborate, 1-butyl-3-methylimidazolium hexafluoroborate, 1-hexyl-3-methylimidazolium hexafluorophosphate, 1-butyl-3-methylimidazolium bis(trifluoromethanesulfonyl)imide, alkylpyridinium tetrafluoroborate, alkylpyridinium hexafluorophosphate, alkylpyridinium bis(trifluoromethanesulfonyl)imide, alkylammonium tetrafluoroborate, alkylammonium hexafluorophosphate, alkylammonium bis(trifluoromethanesulfonyl)imide, N,N-diethyl-N-methyl(2-methoxyethyl)ammonium tetrafluoroborate, N,N-diethyl-N-methyl(2-methoxyethyl)ammonium hexafluorophosphate, and N,N-diethyl-N-methyl(2-methoxyethyl)ammonium bis(trifluoromethanesulfonyl)imide. These ionic liquid species may be used singly or in combination of two or more species. In the case where an ionic liquid has a total acid value higher than 1 mgKOH/g, two or more ionic liquid species are used in combination so as to regulate the total acid value to 1 mgKOH/g or less.

In the present invention, preferred ionic liquid species are alkylpyridinium hexafluorophosphate, alkylpyridinium bis(trifluoromethanesulfonyl)imide, alkylammonium hexafluorophosphate, alkylammonium bis(trifluoromethanesulfonyl)imide, N,N-diethyl-N-methyl(2-methoxyethyl)ammonium hexafluorophosphate, and N,N-diethyl-N-methyl(2-methoxyethyl)ammonium bis(trifluoromethanesulfonyl)imide.

Through employment of two or more ionic liquid species serving as a base oil, a lube oil having remarkably improved physical characteristics (viscosity index, pour point, etc.) can be produced. In this case, these species may be mixed at arbitrary proportions. From the viewpoint of attaining a mixing effect, each ionic liquid species content is preferably adjusted to 10 mass % or more based on the mixture. For example, the mixture contains one $Z^+$ species and two or more $A^-$ species, two or more $Z^+$ species and one $A^-$ species, or two or more $Z^+$ species and two or more $A^-$ species.

Specific examples of the mixture include a mixture of 1-butyl-3-methylimidazolium tetrafluoroborate and 1-butyl-3-methylimidazolium bis(trifluoromethanesulfonyl)imide, a mixture of alkylpyridinium hexafluorophosphate and alkylpyridinium bis(trifluoromethanesulfonyl)imide, a mixture of alkylammonium bis(trifluoromethanesulfonyl)imide and 1-butyl-3-methylimidazolium bis(trifluoromethanesulfonyl)imide, a mixture of 1-butyl-3-methylimidazolium tetrafluoroborate and N,N-diethyl-N-methyl(2-methoxyethyl)ammonium bis(trifluoromethanesulfonyl)imide, a mixture of 1-butyl-3-methylimidazolium hexafluorophosphate and N,N-diethyl-N-methyl(2-methoxyethyl)ammonium bis(trifluoromethanesulfonyl)imide, a mixture of N,N-diethyl-N-methyl(2-methoxyethyl)ammonium bis(trifluoromethanesulfonyl)imide and alkylpyridinium tetrafluoroborate, and a mixture of N,N-diethyl-N-methyl(2-methoxyethyl)ammonium bis(trifluoromethanesulfonyl)imide and alkylpyridinium hexafluorophosphate.

Of these, preferred are a mixture of 1-butyl-3-methylimidazolium tetrafluoroborate and N,N-diethyl-N-methyl(2-methoxyethyl)ammonium bis(trifluoromethanesulfonyl)imide, a mixture of 1-butyl-3-methylimidazolium hexafluorophosphate and N,N-diethyl-N-methyl(2-methoxyethyl)ammonium bis(trifluoromethanesulfonyl)imide, a mixture of N,N-diethyl-N-methyl(2-methoxyethyl)ammonium bis(trifluoromethanesulfonyl)imide and alkylpyridinium tetrafluoroborate, and a mixture of N,N-diethyl-N-methyl(2-methoxyethyl)ammonium bis(trifluoromethanesulfonyl)imide and alkylpyridinium hexafluorophosphate.

Through employment, as a base oil, of an ionic liquid which does not contain a cation (imidazolium) represented by the following formula:

[F12]

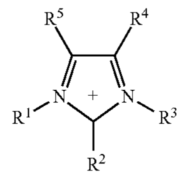

(wherein each of $R^1$ to $R^5$ which may be identical to or different from one another, represents a group selected from among a hydrogen atom, C1 to C18 alkyl groups which may each have an ether bond, and C1 to C18 alkoxy groups), $F^-$, $Cl^-$, $Br^-$, or $BF_4^-$, a non-toxic and non-corrosive lube oil can be produced. Specific examples of such ionic liquid species include alkylpyridinium hexafluorophosphate, alkylpyridinium bis(trifluoromethanesulfonyl)imide, alkylammonium hexafluorophosphate, alkylammonium bis(trifluoromethanesulfonyl)imide, N,N-diethyl-N-methyl(2-methoxyethyl)ammonium hexafluorophosphate, and N,N-diethyl-N-methyl(2-methoxyethyl)ammonium bis(trifluoromethanesulfonyl)imide.

Of these, alkylpyridinium bis(trifluoromethanesulfonyl)imide, alkylammonium bis(trifluoromethanesulfonyl)imide, and N,N-diethyl-N-methyl(2-methoxyethyl)ammonium bis(trifluoromethanesulfonyl)imide are preferred.

In the present invention, there may be employed as a base oil an ionic liquid formed of a zwitter ion in which a cation and an anion are linked via a covalent bond and which has a total acid value of 1 mgKOH/g or less. The amount of the zwitter-ionic liquid is 50 to 100 mass %, preferably 70 to 100 mass %, more preferably 90 to 100 mass %.

For example, the ionic liquid is represented by any of the following formulas:

[F13]

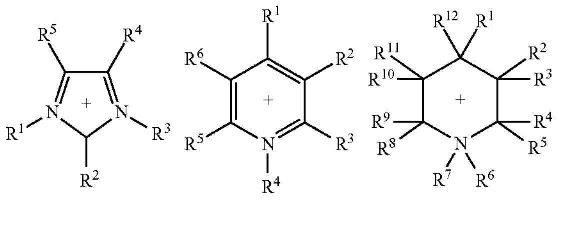

-continued

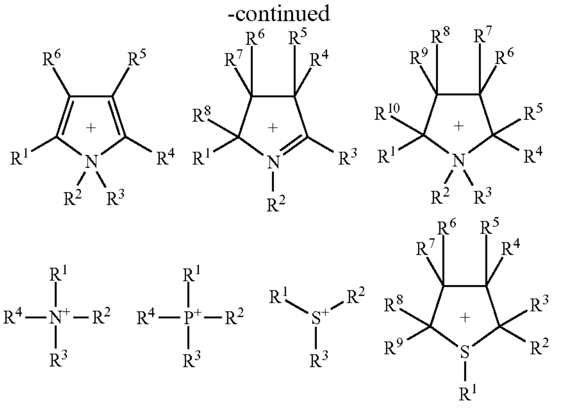

(wherein each of $R^1$ to $R^{12}$, which may be identical to or different from one another, represents a group selected from among a hydrogen atom, C1 to C18 alkyl groups which may each have an ether bond, and C1 to C18 alkoxy groups; and at least one of $R^1$ to $R^{12}$ is $—(CH_2)_n—SO_3^-$ or $—(CH_2)_n—COO^-$ (wherein n is an integer of 0 or greater such that the number of carbon atoms of each alkyl group falls within a range of 1 to 18)).

Specific examples include 1-methyl-1,3-imidazolium-N-butanesulfonate and N,N-diethyl-N-methylammonium-N-butanesulfonate.

From the viewpoint of corrosion prevention of lubrication members, the aforementioned ionic liquid is required to have a total acid value of 1 mgKOH/g or less, preferably 0.5 mgKOH/g or less, more preferably 0.3 mgKOH/g or less.

From the viewpoint of prevention of vaporization loss and power loss due to viscosity resistance, the aforementioned ionic liquid preferably has a kinematic viscosity, as determined at 40° C., of 1 to 1,000 $mm^2/s$, more preferably 2 to 320 $mm^2/s$, further more preferably 5 to 100 $mm^2/s$.

From the viewpoint of prevention of increase in viscosity resistance at low temperature, the aforementioned ionic liquid preferably has pour point of −10° C. or lower, more preferably −20° C. or lower, further more preferably −30° C. or lower.

From the viewpoint of reduction of vaporization loss of base oil, the aforementioned ionic liquid preferably has a flash point of 200° C. or higher, more preferably 250° C. or higher, further more preferably 300° C. or higher.

In order to prevent excessive increase of temperature-dependent viscosity change, the aforementioned ionic liquid preferably has a viscosity index of 80 or higher, more preferably 100 or higher, furthermore, preferably 120 or higher.

The lube oil of the present invention may contain additives so long as the effects of the invention are not impaired. Examples of the additives include antioxidants, oiliness agents, extreme pressure agents, detergent-dispersants, viscosity index improvers, rust preventives, metal deactivators, and defoaming agents. These additive may be used singly or in combination of two or more species.

As antioxidants, amine-based antioxidants, phenol-based antioxidants, and sulfur-based antioxidants, which are employed in conventional hydrocarbon-based lube oils, may be used. These antioxidants may be used singly or in combination of two or more species. Examples of the amine-based anti-oxidants include monoalkyldiphenylamines such as monoctyldiphenylamine and monononyldiphenylamine; dialkyldiphenylamines such as 4,4'-dibutyldiphenylamine, 4,4'-dipentyldiphenylamine, 4,4'-dihexyldiphenylamine, 4,4'-diheptyldiphenylamine, 4,4'-dioctyldiphenylamine, and 4,4'-dinonyldiphenylamine; polyalkyldiphenylamines such as tetrabutyldiphenylamine, tetrahexyldiphenylamine, tetraoctyldiphenylamine, and tetranonyldiphenylamine; and naphtylamines such as α-naphthylamine, phenyl-α-naphtylamine, butylphenyl-α-naphtylamine, pentylphenyl-α-naphtylamine, hexylphenyl-α-naphtylamine, heptylphenyl-α-naphtylamine, octylphenyl-α-naphtylamine, and nonylphenyl-α-naphtylamine.

Examples of the phenol-based anti-oxidants include monophenolic anti-oxidants such as 2,6-di-tert-butyl-4-methylphenol and 2,6-di-tert-butyl-4-ethylphenol; and diphenolic anti-oxidants such as 4,4'-methylenebis(2,6-di-tert-butylphenol) and 2,2'-methylenebis(4-ethyl-6-tert-butylphenol).

Examples of the sulfur-based antioxidants include 2,6-di-tert-butyl-4-(4,6-bis(octylthio)-1,3,5-triazin-2-ylamino)phenol; thioterpene compounds such as reaction products between phosphorus pentasulfide and pinene; and dialkylthio dipropionates such as dilaurylthio dipropionate and distearylthio dipropionate.

The antioxidant(s) are generally incorporated in an amount of about 0.01 to 10 mass % based on the total amount of the lube oil, preferably 0.03 to 5 mass %.

Examples of the oiliness agents include fatty acid compounds such as aliphatic alcohols, fatty acids, and fatty acid metal salts; ester compounds such as polyol esters, sorbitan esters, and glycerides; and amine compounds such as aliphatic amines. The aliphatic alcohols are collectively represented by formula (I):

$$R^{18}—OH \quad (I)$$

(wherein $R^{18}$ represents a group selected from among alkyl groups, alkenyl groups, alkylaryl groups, and arylalkyl groups, each having 8 to 30, preferably 12 to 24 carbon atoms). Examples of the C8 to C30 alkyl groups include octyl groups, nonyl groups, decyl groups, undecyl groups, stearyl groups, lauryl groups, and palmityl groups. Examples of the C8 to C30 alkenyl groups include octenyl, nonenyl, decenyl, and octadecenyl such as oleyl. Examples of the C8 to C30 alkylaryl groups include dimethylphenyl groups, diethylphenyl groups, dipropylphenyl groups, methylnaphthyl groups, and ethylnaphthyl groups. Examples of the C8 to C30 arylalkyl groups include phenethyl and nahpthylmethyl. Of these, stearyl and oleyl are preferred.

The fatty acid compounds are collectively represented by formula (II):

$$(R^{19}—COO)_nX^1 \quad (II)$$

(wherein $R^{19}$ represents a group selected from among alkyl groups, alkenyl groups, alkylaryl groups, and arylalkyl groups, each having 8 to 30, preferably 12 to 24 carbon atoms; $X^1$ represents an atom selected from among H, K, Na, Mg, Ca, Al, Zn, Fe, Cu, and Ag). Examples of the C8 to C30 alkyl groups, alkenyl groups, alkylaryl groups, and arylalkyl groups, each forming $R^{19}$, include the same as described above, and stearyl and oleyl are preferred. $X^1$ is preferably H, K, Al, or Zn. The "n" is an integer of 1 to 3.

Examples of the polyol esters include esterifcation products between a polyhydric alcohol such as neopentyl glycol, trimethylolpropane, or pentaerythritol and a fatty acid represented by formula (III):

$$R^{20}—COOH \quad (III)$$

(wherein $R^{20}$ represents a group selected from among alkyl groups, alkenyl groups, alkylaryl groups, and arylalkyl groups, each having 8 to 30, preferably 8 to 24 carbon atoms). Examples of the group selected from among alkyl groups, alkenyl groups, alkylaryl groups, and arylalkyl groups, each having 8 to 30 carbon atoms and forming $R^{20}$, include the same as described above, and octyl is particularly preferred.

The sorbitan esters are collectively represented by the following formula (IV):

[F14]

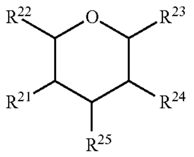

(IV)

(wherein each of $R^{21}$ to $R^{25}$ represents a group selected from H, OH, and $CH_2OCOR^{26}$; $R^{26}$ represents an alkyl or alkenyl group each having 9 to 30, preferably 12 to 24 carbon atoms). Examples of the C9 to 30 alkyl group forming $R^{26}$ include nonyl groups, decyl groups, undecyl groups, stearyl groups, lauryl groups, and palmityl groups. Examples of the C9 to C30 alkenyl group include nonenyl, decenyl, and octadecenyl. Examples of preferred fatty acids include lauric acid, stearic acid, palmitic acid, and oleic acid.

The glycerids are collectively represented by the following formula (V):

[F15]

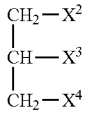

(V)

(wherein each of $X^2$ to $X^4$ represents OH or $OCOR^{27}$; $R^{27}$ represents an alkyl or alkenyl group each having 8 to 30, preferably 12 to 24 carbon atoms). Examples of the C8 to C30 alkyl or alkenyl group forming R include the same as described above. Examples of preferred fatty acids include lauric acid, stearic acid, palmitic acid, and oleic acid.

Examples of the fatty acid amines include mono-substituted, di-substituted, and tri-substituted amines represented by the following formula (VI):

$$R^{28}{}_{m}NH_{3-m} \quad \text{(VI)}$$

(wherein $R^{28}$ represents a group selected from among C3 to C30 (preferably C8 to C24) alkyl and alkenyl groups, C6 to C30 (preferably C6 to C15) aryl and arylalkyl groups, and C2 to C30 (preferably C2 to C18) hydroxyalkyl groups; and m is an integer of 1 to 3). Among these groups, the alkyl and alkenyl groups each forming $R^{28}$ may be linear, branched, or cyclic. Examples of the C3 to C30 alkyl and alkenyl groups, and examples of C6 to C30 aryl and arylalkyl groups include the same as described above. Examples of the C2 to C30 hydroxyalkyl group include hydroxyethyl and hydroxypropyl.

From the effect of incorporation, these oiliness agent(s) are generally incorporated in an amount of about 0.1 to 30 mass % based on the total amount of the lube oil, preferably 0.5 to 10 mass %.

Examples of the extreme pressure agent include sulfur-containing agents, phosphorus-containing agents, agents containing sulfur and metal, and agents containing phosphorus and metal. These extreme pressure agents may be used singly or in combination of two or more species. Any extreme pressure agent may be used, so long as the agent contains in the molecule thereof a sulfur atom and/or a phosphorus atom and can exhibit load resistance and wear resistance. Examples of the extreme pressure agent containing a sulfur atom in the molecule thereof include sulfidized fats and oils, sulfidized fatty acid, sulfidized esters, sulfidized olefins, dihydrocarbyl polysulfides, thiadiazole compounds, alkyl thiocarbamoyl compounds, triazine compounds, thioterpene compounds, and dialkyl thiodipropionate compounds.

The sulfidized fats and oils are produced through reaction of a fat or an oil (e.g., lard, whale oil, vegetable oil, or fish oil) with sulfur or a sulfur-containing compound. Although no particular limitation is imposed on the sulfur content, the content preferably 5 to 30 mass %. Specific examples include sulfidized lard, sulfidized rape seed oil, sulfidized castor oil, sulfidized soy bean oil, and sulfidized rice bran oil. Examples of the sulfidized fatty acids include sulfidized oleic acid. Examples of the sulfidized esters include sulfidized methyl oleate and sulfidized octyl ester of rice bran fatty acid.

Examples of the sulfidized olefins include compounds represented by the following formula (VII):

$$R^{29}—S_a—R^{30} \quad \text{(VII)}$$

(wherein $R^{29}$ represents a C2 to C15 (preferably C4 to C8) alkenyl group, $R^{30}$ represents a C2 to C15 (preferably C4 to C8) alkyl group or alkenyl group; and a is an integer of 1 to 8, preferably 1 to 3). These compounds are produced reaction between a C2 to C15 olefin or a dimer to tetramer thereof and a sulfidizing agent such as sulfur or sulfur chloride. Preferred C2 to C15 olefins include propylene, isobutene, and diisobutene.

Examples of the dihydrocarbyl polysulfides include compounds represented by the following formula (VIII):

$$R^{31}—S_b—R^{32} \quad \text{(VIII)}$$

(wherein $R^{31}$ and $R^{32}$, which may be identical to or different from each other, each represents a C1 to C20 (preferably C4 to C18) alkyl group or cyclic alkyl group, a C6 to C20 (preferably C6 to C15) aryl group, a C7 to C20 (preferably C7 to C15) alkyl aryl group, or a C7 to C20 (preferably C7 to C15) arylalkyl group; and b is an integer of 2 to 8, preferably 2 to 4). When each of $R^{31}$ and $R^{32}$ an alkyl group, the compound is called alkyl sulfide.

Examples of the group represented by $R^{31}$ or $R^{32}$ in formula (VIII) include methyl, ethyl, n-propyl, isopropyl, n-butyl, isobutyl, sec-butyl, tert-butyl, pentyl groups, hexyl groups, heptyl groups, octyl groups, nonyl groups, decyl groups, dodecyl groups, cyclohexyl, cyclooctyl, phenyl, naphthyl, tolyl, xylyl, benzyl, and phenetyl.

Examples of preferred dihydrocarbyl polysulfides include dibenzyl polysulfides, dinonyl polysulfides, didodecyl polysulfides, dibutyl polysulfides, dioctyl polysulfides, diphenyl polysulfides, and dicyclohexyl polysulfided.

Examples of preferably employed thiadiazole compounds include 1,3,4-thiadiazole, 1,2,4-thiadiazole compound, and 1,4,5-thiadiazole represented by the following formula (IX) or (X):

[F16]

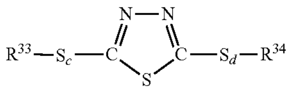

(IX)

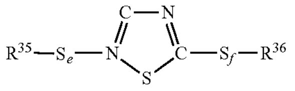

(X)

(wherein each of $R^{33}$ to $R^{36}$ represents a hydrogen atom, a C1 to C20 (preferably C4 to C13) hydrocarbon group; and each of c to f is an integer of 0 to 8, preferably 1 to 4). Specific examples of preferred thiadiazole compounds include 2,5-bis(n-hexyldithio)-1,3,4-thiadiazole, 2,5-bis(n-octyldithio)-1,3,4-thiadiazole, 2,5-bis(n-honyldithio)-1,3,4-thiadiazole, 2,5-bis(1,1,3,3-tetramethylbutyldithio)-1,3,4-thiadiazole, 3,5-bis(n-hexyldithio)-1,2,4-thiadiazole, 3,5-bis(n-octyldithio)-1,2,4-thiadiazole, 3,5-bis(n-nonyldithio)-1,2,4-thiadiazole, and 3,5-bis(1,1,3,3-tetramethylbutyldithio)-1,2,4-thiadiazole.

Examples of preferably employed alkyl thiocarbamoyl compounds include compounds represented by the following formula (XI):

[F17]

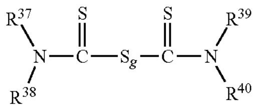

(XI)

(wherein each of $R^{37}$ to $R^{40}$ represents a C1 to C20 (preferably C4 to C8) alkyl group, and g is an integer of 1 to 8, preferably 1 to 3). Specific examples of preferred alkyl thiocarbamoyl compounds include bis(dimethylthiocarbamoyl) monosulfide, bis(dibutylthiocarbamoyl) monosulfide, bis(dimethylthiocarbamoyl) disulfide, bis(dibutylthiocarbamoyl) disulfide, bis(diamylthiocarbamoyl) disulfide, and bis(octylthiocarbamoyl) disulfide.

Examples of the extreme pressure agent containing sulfur or phosphorus with metal include zinc dialkylthiocarbamate (Zn-DTC), molybdenum dialkylthiocarbamate (Mo-DTC), lead dialkylthiocarbamate, tin dialkylthiocarbamate, zinc dialkylthiophosphate (Zn-DTP), molybdenum dialkylthiophosphate (Mo-DTP), sodium sulfonate, and calcium sulfonate.

Typical examples of the extreme pressure agent containing phosphorus in the molecule thereof are phosphate esters and amine salts thereof. The phosphate esters include phosphate esters, acid phosphate esters, phosphite esters, and acid phosphite esters represented by the following formulas (XII) to (XVI):

[F18]

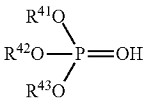

(XII)

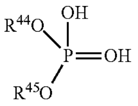

(XIII)

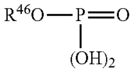

(XIV)

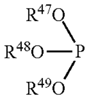

(XV)

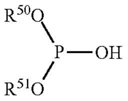

(XVI)

(wherein $R^{41}$ to $R^{51}$, which may be identical to or different from one another, each represents an alkyl group, an alkenyl group, an alkylaryl group, or an arylalkyl group, having 4 to 30 (preferably 4 to 18) carbon atoms).

Examples of the phosphate esters include triaryl phosphates, trialkyl phosphates, trialkylaryl phosphates, triarylalkyl phosphates, and trialkenyl phosphates. Specific examples include triphenyl phosphate, tricresyl phosphate, benzyl diphenyl phosphate, ethyl diphenyl phosphate, tributyl phosphate, ethyl dibutyl phosphate, cresyl diphenyl phosphate, dicresyl phenyl phosphate, ethylphenyl diphenyl phosphate, diethylphenyl phenyl phosphate, propylphenyl diphenyl phosphate, dipropylphenyl phenyl phosphate, triethylphenyl phosphate, tripropylphenyl phosphate, butylphenyl diphenyl phosphate, dibutylphenyl phenyl phosphate, tributylphenyl phosphate, trihexyl phosphate, tri(2-ethylhexyl) phosphate, tridecyl phosphate, trilauryl phosphate, trimyristyl phosphate, tripalmityl phosphate, tristearyl phosphate, and trioleyl phosphate.

Examples of the acid phosphate esters include 2-ethylhexyl acid phosphate, ethyl acid phosphate, butyl acid phosphate, oleyl acid phosphate, tetracosyl acid phosphate, isodecyl acid phosphate, lauryl acid phosphate, tridecyl acid phosphate, stearly acid phosphate, and isostearyl acid phosphate.

Examples of the phosphite esters include triethyl phosphite, tributyl phosphite, triphenyl phosphite, trieresyl phosphite, tri(nonylphenyl) phosphite, tri(2-ethylhexyl) phosphite, tridecyl phosphite, trilauryl phosphite, triisooctyl phosphite, diphenyl isodecyl phosphite, tristearyl phosphite, and trioleyl phosphite.

Examples of the acid phosphite esters include dibutyl hydrogen phosphite, dilauryl hydrogen phosphite, dioleyl hydrogen phosphite, distearyl hydrogen phosphite, and diphenyl hydrogen phosphite. Examples of the amines which form amine salts with the phosphate esters include monosubstituted amines, disubstituted amines, and trisubstituted amines, which are represented by formula (XVII):

$$R^{52}{}_{h}NH_{3}\text{-}h \quad \text{(XVII)}$$

(wherein $R^{52}$ represents a C3 to C30 (preferably C4 to C18) alkyl group or alkenyl group, a C6 to C30 (preferably C6 to C15) aryl group or arylalkyl group, or a C2 to C30 (preferably C2 to C18) hydroxyalkyl group; h is 1, 2, or 3; when a plurality of $R^{52}$ s are present, these $R^{52}$ s may be identical to or different from one another). The C3 to C30 alkyl or alkenyl group represented by $R^{52}$ in the above formula (XVII) may be linear, branched, or cyclic.

Examples of the monosubstituted amines include butylamine, pentylamine, hexylamine, cyclohexylamine, octylamine, laurylamine, stearylamine, oleylamine, and benzylamine. Examples of the disubstituted amines include dibutylamine, dipentylamine, dihexylamine, dicyclohexylamine, dioctylamine, dilaurylamine, distearylamine, dioleylamine, dibenzylamine, stearylmonoethanolamine, decylmonoethanolamine, hexylmonopropanolamine, benzylmonoethanolamine, phenylmonoethanolamine, and tolylmonopropanol. Examples of the trisubstituted amines include tributylamine, tripentyl amine, trihexylamine, tricyclohexylamine, trioctylamine, trilaurylamine, tristearylamine, trioleylamine, tribenzylamine, dioleylmonoethanolamine, dilaurylmonopropanolamine, dioctylmonoethanolamine, dihexylmonopropanolamine, dibutylmonopropaolamine, oleyldiethanolamine, stearyldipropanolamine, lauryldiethanolamine, octyldipropanolamine, butyldiethanolamine, benzyldiethanolamine, phenyldiethanolamine, tolyldipronanolamine, xylyldiethanolamine, triethanolamine, and tripropanolamine.

From the viewpoint of the effect of addition and cost, these extreme pressure agent(s) may be incorporated generally in an amount of about 0.01 to 30 mass % based on the total amount of the composition, more preferably 0.01 to 10 mass %.

Examples of the detergent-dispersant include metal sulfonates, metal salicylates, metal phenates, and succinimide. From the viewpoint of the effect of addition, the detergent-dispersant(s) are incorporated generally in an amount of about 0.1 to 30 mass % based on the total amount of the composition, preferably 0.5 to 10 mass %.

Examples of the viscosity index improver include polymethacrylates, dispersion-type polymethacrylates, olefin copolymers (e.g., ethylene-propylene copolymer), dispersion-type olefin copolymers, and styrene copolymers (e.g., styrene-diene hydrogenated copolymer).

From the viewpoint of the effect of addition, the viscosity index improver(s) are preferably incorporated generally in an amount of about 0.5 to 35 mass % based on the total amount of the lube oil, preferably 1 to 15 mass %.

Examples of rust preventives include metal sulfonates and succinate esters. From the viewpoint of the effect of addition, the rust preventive(s) are incorporated generally in an amount of about 0.01 to 10 mass % based on the total amount of the lube oil, preferably 0.05 to 5 mass %.

Examples of the metal deactivator include benzotriazoles and thiadiazoles. From the viewpoint of the effect of addition, the metal deactivator(s) are preferably incorporated generally in an amount of about 0.01 to 10 mass % based on the total amount of the lube oil, preferably 0.01 to 1 mass %.

Examples of the defoaming agent include methylsilicone oil, fluorosilicone oil, and polyacrylate. From the viewpoint of the effect of addition, the defoaming agent(s) are incorporated generally in an amount of about 0.0005 to 0.01 mass % based on the total amount of the lube oil.

The lube oil of the present invention may employ an additional base oil in combination, so long as the effects of the invention are not impaired. The additional base oil may be appropriately selected from mineral oils and synthetic oils. Examples of the mineral oils include distillates obtained through distillation under normal pressure of paraffin base crude, intermediate base crude, or naphthene base crude; distillates obtained through distillation under reduced pressure of normal-pressure distillation residue; and refined oils obtained from the distillates through a routine refining process. Specific examples include solvent-refined oil, hydrorefined oil, dewaxed oil, and clay-treated oil.

Examples of the synthetic oils include low-molecular-weight polybutene, low-molecular-weight polypropylene, C8 to C14 $\alpha$-olefin oligomers, and hydrogenated products thereof; ester compounds such as polyol esters (e.g., trimethylolpropane fatty acid esters and pentaerythritol fatty acid esters), dibasic acid esters, aromatic polypropylenecarboxylic acid esters (e.g., trimellitic acid esters and pyromellitic acid esters), and phosphate esters; alkyl aromatic compounds such as alkylbenzenes and alkylnaphthalenes; silicone oils; polyphenyl; alkyl-substituted diphenyl ethers; polyphenyl ethers; phosphazene compounds; and fluorocarbon oils (e.g., fluorocarbon and perfluoropolyether).

These additional base oils may be used singly or in combination of two or more species.

In order to prevent drop in viscosity and corrosion, the lube oil of the present invention preferably has a water content of 3,000 ppm by mass or less based on the amount of lube oil, more preferably 500 ppm by mass or less, particularly preferably 100 ppm by mass or less. Use of non-aqueous ionic liquid is preferred so as to adjust the water content of the lube oil to 500 ppm by mass.

Through employment of electrical properties of the ionic liquid contained in the lube oil of the present invention, cations and anions can be intentionally adsorbed on a friction surface through application of an electric field to the lube oil, thereby forming a lubrication protective film. The lubrication protective film enables regulation of characteristics of lube oil such as tribological characteristics. No particular limitation is imposed on the way of electric field application. For example, there may be employed method (1) including filling a friction site with a lube oil, the friction site being provided between two friction members sliding relative to each other, disposing electrodes in a non-contact manner such that the friction site intervenes therebetween, and applying voltage to the lube oil, and method (2) including filling a friction site with a lube oil, the friction site being provided between two friction members made of conductive material and sliding relative to each other, and applying voltage directly to the two friction members. From the viewpoint of safety, cost, and the effect of application, applied voltage is generally about 0.1 to $5\times10^{6}$ mV, preferably 0.1 to $5\times10^{3}$ mV, more preferably 0.1 to 100 mV. The applied voltage may be DC or AC.

Through employment of the lube oil of the present invention, a lubrication characteristic regulating apparatus for regulating lubrication characteristics of a contact region between two lubrication members can be fabricated. In the lubrication characteristic regulating apparatus, the lube oil of the present invention is present in the contact region between two lubrication members, and a pair of electrodes which are placed so as to sandwich the contact region are provided such that the electrodes are in contact or are not in contact with the lubrication members.

In the case where one or two of the lubrication members of the lubrication characteristic regulating apparatus of the present invention are formed of non-conductive material, the electric field line pattern is provided such that the electric field lines penetrate the contact region from one electrode to the other electrode. Alternatively, such an electric field line pattern may predominate over other electric field line patterns. In the case where two lubrication members are formed of conductive material, the electric field line pattern is provided such that the electric field lines run from one electrode to the other electrode sequentially via one lubrication member, the contact region, and the other second lubrication member. Alternatively, such an electric field line pattern may predominate over other electric field line patterns.

In an operation of the lubrication characteristic regulating apparatus of the present invention, a contact region between two lubrication members is filled with a lube oil, and an electric field is applied to the lube oil by means of a pair of electrodes. Through electric field application, an electric field line pattern is formed from one electrode to the other electrode sequentially via one lubrication member, the contact region, and the other lubrication member along with other electric field line patterns. Thus, internal shear stress in the lube oil present in the lubrication region varies in accordance with change in voltage, leading to change in lubrication characteristics observed as change in viscosity.

EXAMPLES

The present invention will next be described in more detail by way of examples, which should not be construed as limiting the invention thereto. Characteristics of lube oils were determined through the following procedure.

(1) Kinematic Viscosity

Determined in accordance with "Kinematic viscosity test for petroleum products" as stipulated in JIS K2283

(2) Viscosity Index

Determined in accordance with "Kinematic viscosity test for petroleum products" as stipulated in JIS K2283

(3) Pour Point

Determined in accordance with JIS K2269

(4) Total Acid Value

Determined through potentiometry in accordance with "Lube oil neutralization test" as stipulated in JIS K2501

(5) Flash Point

Determined through the C.O.C method in accordance with JIS K2265

(6) Water Content

Determined in accordance with JIS K2275

(7) 5% Mass Reduction Temperature

The temperature at which mass of a sample was reduced from the initial mass by 5% was determined by means of a differential thermal analyzer under a 10° C./min temperature elevation condition. Higher 5% mass reduction temperature indicates excellent resistance to vaporization and heat resistance.

(8) Corrosion Property

A slip form cut iron (purity: 99.9%) sheet was immersed in each sample (10 mL), and allowed to stand at 100° C. for three hours. Thereafter, appearance of the iron sheet was observed, and the difference in mass of the iron sheet between before immersion and after immersion was calculated.

(9) Triboligical Characteristics (I)

A ball-on-disk tribological test was performed by means of a pin disk tester (product of CSEM) under the conditions of room temperature, load: 20N, sliding speed: 0.5 m/s, and test time 30 min. Test pieces (balls and disks) made of SUJ-2 were employed. Mean friction coefficient (μ) and ball wear track diameter were determined. Smaller mean friction coefficient (μ) and ball wear track diameter indicate excellent tribological characteristics.

(10) Triboligical Characteristics (II)

Variation in friction coefficient in the presence or absence of voltage application was evaluated by means of a ball-on-disk type reciprocal tribological tester under the conditions of 75° C., load: 20N, frequency: 1 Hz, and sliding distance: 5 mm. Test pieces (balls and disks) made of SUJ-2 were employed. Voltage (100 mV) was applied, and mean friction coefficients (μ) 5 min after and 15 min after the start of the test were determined.

(11) Ion Concentration of Base Oil

Density and molecular weight (Mw) of Ionic liquids 1 to 4 were determined at 20° C., and each ion concentration was calculated from the relationship: [density of ionic liquid ($g/cm^3$)/molecular weight (MW) of ionic liquid (g/mol)]×1000. Ionic liquids 1 to 4 were found to have a density and a molecular weight (Mw) of 1.283 $g/cm^3$ and 197.97 g/mol (Ionic liquid 1), 1.453 $g/cm^3$ and 416.36 g/mol (Ionic liquid 2), 1.420 $g/cm^3$ and 426.40 g/mol (Ionic liquid 3), and 1.208 $g/cm^3$ and 226.02 g/mol (Ionic liquid 4), respectively.

Examples 1 to 5 and Comparative Examples 1 to 7

Lube oils were prepared from ingredients listed in Table 1, and each sample was evaluated in terms of the aforementioned characteristics. The results are shown in Table 1.

TABLE 1

Table 1-1

| | Ingredients (mass %) | Ex. 1 | Ex. 2 | Ex. 3 | Ex. 4 | Ex. 5 | Comp. Ex. 1 |
|---|---|---|---|---|---|---|---|
| Base oils | Ionic liquid 1 | | | | | | 100 |
| | Ionic liquid 2 | 100 | | | | | |
| | Ionic liquid 3 | | 100 | 99 | 99 | 98 | |
| | Ionic liquid 4 | | | | | | |
| | Polyα-olefin | | | | | | |
| | Polyol polyester | | | | | | |
| | Aromatic ester | | | | | | |
| | Perfluoropoly ether | | | | | | |
| Additives | Amine-based antioxidant | | | | | 1 | |
| | TCP | | | 1 | | | |
| | DBDS | | | | 1 | 1 | |
| Evaluation | Kinematic viscosity (40° C.) ($mm^2/s$) | 22.41 | 27.10 | 27.14 | 27.10 | 27.31 | 18.06 |
| | Viscosity Index | 160 | 114 | 114 | 114 | 114 | 111 |
| | Pour point (° C.) | −20.0 | −30.0 | −30.0 | −30.0 | −32.5 | 0 |

TABLE 1-continued

Table 1-1

| Ingredients (mass %) | | Ex. 1 | Ex. 2 | Ex. 3 | Ex. 4 | Ex. 5 | Comp. Ex. 1 |
|---|---|---|---|---|---|---|---|
| Total acid value (mgKOH/g) | | 0.29 | 0.30 | 0.32 | 0.30 | 0.33 | 25 |
| Flash point (C.O.C) | | 300< | 300< | 300< | 300< | 300< | 300< |
| Aqueous (AQ) or Nonaqueous (NA) | | NA | NA | NA | NA | NA | AQ |
| Water content (mass ppm) | | 23 | 19 | 21 | 21 | 23 | 876 |
| DTA (5% mass reduction temp.) (° C.) | | 411.3 | 363.8 | 362.5 | 361.1 | 361.3 | 381.0 |
| Corrosion | Appearance | No color change | No color change | No color change | No color change | No color change | Color changed |
| | Mass reduction (mg) | 0.1> | 0.1> | 0.1> | 0.1> | 0.1> | 5.4 |
| Triboligical properties (I) | Mean friction coeff. (μ) | 0.075 | 0.086 | 0.080 | 0.077 | 0.075 | 0.034 |
| | Ball wear track diam. (mm) | 0.48 | 0.50 | 0.48 | 0.44 | 0.46 | 0.47 |
| Toxicity | | No | No | No | No | No | Yes |
| Ion concentration of base oil (20° C.) (mol/dm$^3$) | | 6.48 | 3.33 | — | — | — | 6.48 |

TABLE 2

Table 1-2

| Ingredients (mass %) | | | Comp. Ex. 2 | Comp. Ex. 3 | Comp. Ex. 4 | Comp. Ex. 5 | Comp. Ex. 6 | Comp. Ex. 7 |
|---|---|---|---|---|---|---|---|---|
| Base oils | Ionic liquid 1 | | | | | | | |
| | Ionic liquid 2 | | | | | | | |
| | Ionic liquid 3 | | | | | | | |
| | Ionic liquid 4 | | | | | | | 100 |
| | Polyα-olefin | | 100 | 99 | | | | |
| | Polyol polyester | | | | 100 | | | |
| | Aromatic ester | | | | | 100 | | |
| | Perfluoropoly ether | | | | | | 100 | |
| Additives | Amine-based antioxidant | | | | | | | |
| | TCP | | | 1 | | | | |
| | DBDS | | | | | | | |
| Evaluation | Kinematic viscosity (40° C.) (mm$^2$/s) | | 16.80 | 17.30 | 19.50 | 40.20 | 17.00 | 42.54 |
| | Viscosity Index | | 124 | 130 | 132 | 137 | 253 | 152 |
| | Pour point (° C.) | | −50> | −50> | −45 | −50> | −50> | −40 |
| | Total acid value (mgKOH/g) | | 0.01> | 0.01> | 0.05 | 0.01 | 0.01> | 1.05 |
| | Flash point (C.O.C) | | 215 | 224 | 236 | 291 | 300< | 300 |
| | Aqueous (AQ) or Nonaqueous (NA) | | NA | NA | NA | NA | NA | AQ |
| | Water content (mass ppm) | | 45 | 52 | 71 | 112 | 20 | 756 |
| | DTA (5% mass reduction temp.) (° C.) | | 233.6 | 246.0 | 269.3 | 297.4 | 225.0 | 340.2 |
| | Corrosion | Appearance | No color change | No color change | No color change | No color change | No color change | Color changed |
| | | Mass reduction (mg) | 0.1> | 0.1> | 0.1> | 0.1> | 0.1> | 3.7 |
| | Triboligical properties (I) | Mean friction coeff. (μ) | 0.140 | 0.090 | 0.080 | 0.082 | 0.160 | 0.045 |
| | | Ball wear track diam. (mm) | 0.49 | 0.41 | 0.43 | 0.44 | 0.55 | 0.045 |
| | Toxicity | | No | No | No | No | No | Yes |
| Ion concentration of base oil (20° C.) (mol/dm$^3$) | | | 0 | — | 0 | 0 | 0 | 5.34 |

(Note)

Ionic liquid 1: 1-Ethyl-3-methylimidazolium tetrafluoroborate

Ionic liquid 2: Butylpyridinium bis(trifluoromethanesulfonyl)imide

Ionic liquid 3: N,N-diethyl-N-methyl(2-methoxyethyl)ammonium bis(trifluoromethanesulfonyl)imide Ionic liquid 4: 1-Butyl-3-methylimidazolium tetrafluoroborate Polyα-olefin: 1-Decene oligomer Polyol polyester: Trimethylolpropane C8, C10 fatty acid ester Aromatic ester: Tri(n-octyl) trimellitate Perfluoropoly ether: Fomblin MO3 (product of Solvat Solexis)

Amine-based antioxidant: 4,4-Dibutyldiphenylamine

TCP: Tricresyl phosphate

DBDS: Dibenzyl disulfide

Toxicity: A compound exhibiting an LD50 (rats, peroral) of 30 to 300 mg/kg, equivalent to a deleterious substance as stipulated in the poisonous and deleterious substances control law, was evaluated to be toxic.

As is clear from Table 1, the lube oil samples of Examples 1 to 5 have a flash point of 300° C. or higher despite low viscosity, and exhibit high 5% mass reduction temperature as determined through differential thermal analysis (DTA), indicating that these lube oil samples have excellent vaporization resistance and heat resistance. In addition, the lube oil samples of Examples 1 to 5 exhibit small friction coefficient and ball wear track diameter, indicating that these lube oil samples have excellent tribological characteristics.

In contrast, the lube oil samples of Comparative Examples 1 and 7, each containing an ionic liquid having a total acid value greater than 1 mgKOH/g, are highly corrosive, although they have excellent heat resistance and wear resistance. Thus, these samples are not suited for lube oils for metallic articles.

Examples 6 to 15

Lube oils were prepared from ingredients listed in Table 2, and each sample was evaluated in terms of the aforementioned characteristics. The results are shown in Table 2.

(Note)

Ionic liquid 5: N,N-diethyl-N-methyl(2-methoxyethyl)ammonium tetrafluoroborate

Ionic liquid 6: Butylpyridinium bis(trifluoromethanesulfonyl)imide

Amine-based antioxidant: 4,4-Dibutyldiphenylamine

TCP: Tricresyl phosphate

DBDS: Dibenzyl disulfide

TABLE 3

Table 2-1

| Ingredients (mass %) | | | Ex. 6 | Ex. 7 | Ex. 8 | Ex. 9 | Ex. 10 |
|---|---|---|---|---|---|---|---|
| Base oils | Ionic liquid 5 | | 90 | 80 | 60 | 50 | 40 |
| | Ionic liquid 6 | | 10 | 20 | 40 | 50 | 60 |
| Additives | Amine-based antioxidant | | | | | | |
| | TCP | | | | | | |
| Evaluation | Kinematic viscosity (40° C.) ($mm^2$/s) | | 65.39 | 45.73 | 44.46 | 38.65 | 35.31 |
| | Viscosity Index | | 17 | 162 | 130 | 143 | 160 |
| | Pour point (° C.) | | −27.5 | −37.5 | −35.0 | −45.0 | −37.5 |
| | Total acid value (mgKOH/g) | | 0.08 | 0.11 | 0.15 | 0.18 | 0.20 |
| | Flash point (C.O.C) | | 300< | 300< | 300< | 300< | 300< |
| | DTA (5% mass reduction temp.) (° C.) | | 373.2 | 380.2 | 397.6 | 401.4 | 405.1 |
| | Corrosion | Appearance | No color chang | No color change | No color change | No color change | No color change |
| | | Mass reduction (mg) | 0.1> | 0.1> | 0.1> | 0.1> | 0.1> |
| | Triboligical properties (I) | Mean friction coeff. (μ) | 0.075 | 0.079 | 0.080 | 0.077 | 0.075 |
| | | Ball wear track diam. (mm) | 0.48 | 047 | 0.45 | 0.44 | 0.46 |

TABLE 4

Table 2-2

| Ingredients (mass %) | | | Ex. 11 | Ex. 12 | Ex. 13 | Ex. 14 | Ex. 15 |
|---|---|---|---|---|---|---|---|
| Base oils | Ionic liquid 5 | | 20 | 10 | 49 | 100 | |
| | Ionic liquid 6 | | 80 | 90 | 49 | | 100 |
| Additives | Amine-based antioxidant | | | | 1 | | |
| | TCP | | | | 1 | | |
| Evaluation | Kinematic viscosity (40° C.) ($mm^2$/s) | | 25.73 | 24.63 | 34.12 | 85.29 | 22.41 |
| | Viscosity Index | | 185 | 162 | 143 | 123 | 160 |
| | Pour point (° C.) | | −40.0 | −27.5 | −45.0 | −7.5 | −20.0 |
| | Total acid value (mgKOH/g) | | 0.24 | 0.27 | 0.19 | 0.06 | 0.29 |
| | Flash point (C.O.C) | | 300< | 300< | 300< | 300< | 300< |
| | DTA (5% mass reduction temp.) (° C.) | | 407.0 | 408.9 | 396.5 | 372.0 | 411.3 |
| | Corrosion | Appearance | No color chang | No color change | No color change | No color change | No color change |
| | | Mass reduction (mg) | 0.1> | 0.1> | 0.1> | 0.1> | 0.1> |
| | Triboligical properties (I) | Mean friction coeff. (μ) | 0.081 | 0.077 | 0.073 | 0.080 | 0.072 |
| | | Ball wear track diam. (mm) | 0.47 | 046 | 0.36 | 0.43 | 0.44 |

As is clear from Table 2, combination use of two types of ionic liquids improves viscosity index and pour point, as compared with single use of lube oil.

Examples 16 and 17 and Comparative Examples 8 and 9

Lube oils were prepared from ingredients listed in Table 3, and each sample was evaluated in terms of the aforementioned characteristics. The results are shown in Table 3.

TABLE 5

Table 3

| Ingredients (mass %) | | | Ex. 16 | Ex. 17 | Comp. Ex. 8 | Comp. Ex. 9 |
|---|---|---|---|---|---|---|
| Base oil | Ionic liquid 3 | | 100 | 98 | 100 | 98 |
| Additives | Amine-based antioxidant | | | 1 | | 1 |
| | TCP | | | 1 | | 1 |
| Evaluation | Kinematic viscosity (40° C.) ($mm^2/s$) | | 27.10 | 27.31 | 27.10 | 27.31 |
| | Viscosity index | | 114 | 114 | 114 | 114 |
| | Pour point (° C.) | | −30.0 | −45.0 | −30.0 | −45.0 |
| | Total acid value (mgKOH/g) | | 0.30 | 0.33 | 0.30 | 0.33 |
| | Flash point (C.O.C) | | 300< | 300< | 300< | 300< |
| | DTA (5% mass reduction temp.) (° C.) | | 363.8 | 361.3 | 363.8 | 361.3 |
| | Corrosion | Appearance | No color change | No color change | No color change | No color change |
| | | Mass reduction (mg) | 0.1> | 0.1> | 0.1> | 0.1> |
| | Tribological properties (II) | Voltage application (100 mV) | Yes | Yes | No | No |
| | | Mean friction coeff. (μ) 5 min after | 0.112 | 0.10 | 0.140 | 0.136 |
| | | Mean friction coeff. (μ) 10 min after | 0.134 | 0.132 | 0.176 | 0.171 |

(Note)

Ionic liquid 3: N,N-diethyl-N-methyl(2-methoxyethyl)ammonium bis(trifluoromethanesulfonyl)imide Amine-based antioxidant: 4,4-Dibutyldiphenylamine TCP: Tricresyl phosphate As is clear from Table 3, comparison of Example 16 with Comparative Example 8 and comparison of Example 17 with Comparative Example 9 indicate that tribological characteristics of lube oil can be improved through application of an electric field thereto.

INDUSTRIAL APPLICABILITY

The lube oil of the present invention is suitably used in internal combustion engines, torque converters, radial bearings, rolling bearings, oil-retaining bearings, fluid bearings, compressors, chain drives, gears, oil hydraulic circuits, vacuum pumps, clock parts, hard disk apparatuses, refrigerators, cutting, rolling, metal drawing, form rolling, forging, heat treatment, heat media, cooling media, coolants, washing, shock absorbers, corrosion prevention, brake members, sealing devices, and aerospace apparatuses such as aircraft and artificial satellites.

The invention claimed is:

1. A method of lubricating an article, comprising providing to the article a lube oil, wherein the lube oil comprises, as a base oil, an ionic liquid having an ion concentration of 1 $mol/dm^3$ or more in an amount of 90 to 100 mass %, wherein the ionic liquid has a total acid value of 1 mgKOH/g or less and is represented by the formula $Z^+A^-$ where $Z^+$represents a cation and $A^-$ represents an anion;

at least one of an antioxidant and an extreme pressure agent, wherein the cation ($Z^+$) forming the ionic liquid is represented by any of the following formulae:

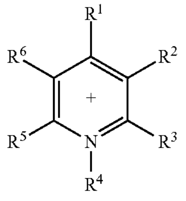

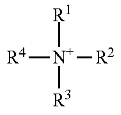

-continued

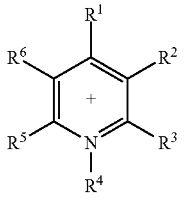

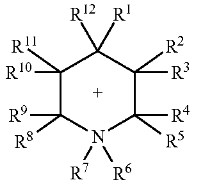

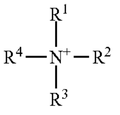

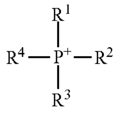

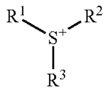

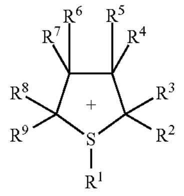

wherein each of $R^1$ to $R^6$, which may be identical to or different from one another, represents a group selected from among a hydrogen atom, C1 to C18 alkyl groups which may each have an ether bond, and C1 to C18 alkoxy groups, wherein the anion ($A^-$) forming the ionic liquid is $BF_4^-$ or $((C_nF_{2n+1-x})H_x)Y^1O_z)_2N^-$, wherein $Y^1$ represents a carbon atom or a sulfur atom, wherein a plurality of $Y^1$ are present, these may be identical or different from one another, a plurality of $(C_nF_{2n+1-x})H_x)Y^1O_z$ groups may be identical or different from one another, n is an integer of from 1 to 6, x is an integer of from 0 to 13, and z is an integer of from 1 to 3 when $Y^1$ is a carbon atom and 0 to 4 when $Y^1$ is a sulfur atom, and wherein the article is an internal combustion engine, a torque converter, a fluid coupling, a radial bearing, a rolling bearing, an oil-retaining bearing, a fluid bearing, a compressor, a chain drive, a vacuum pump, a clock part, a hard disk apparatus, a refrigerator, a shock absorber, a corrosion prevention, a brake member, a sealing device, or an aerospace apparatus.

2. The method as claimed in claim 1, wherein the ionic liquid is a mixture of two or more ionic liquids.

3. The method as claimed in claim 1, wherein the ionic liquid does not contain a cation represented by the following formula:

[F6]

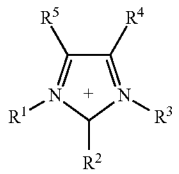

(wherein each of $R^1$ to $R^5$, which may be identical to or different from one another, represents a group selected from among a hydrogen atom, C1 to C18 alkyl groups which may each have an ether bond, and C1 to C18 alkoxy groups), $F^-$, $Cl^-$, $Br^-$, or $BF_4^-$.

4. The method as claimed in claim 1, wherein the ionic liquid has a kinematic viscosity of 1 to 1,000 $mm^2/s$ as determined at 40° C.

5. The method as claimed in claim 1, wherein the ionic liquid has a pour point of −10° C. or lower.

6. The method as claimed in claim 1, wherein the ionic liquid has a viscosity index of 80 or more.

7. The method as claimed in claim 1, wherein the ionic liquid has a flash point of 200° C. or higher.

8. The method as claimed in claim 1, further comprising applying an electric field to the lube oil.

9. The method as claimed in claim 1, wherein the lube oil has a total acid value of 0.33 mgKOH/g or less.

10. The method of claim 1, wherein the ionic liquid is butylpyridinium bis(trifluoromethanesulfonyl)imide, N,N-diethyl-N-methyl(2-methoxyethyl)ammonium bis(trifluoromethanesulfonyl)imide, or N,N-diethyl-N-methyl(2-methoxyethyl)ammonium tetrafluoroborate.

* * * * *